United States Patent [19]

Moret et al.

[11] 4,146,020
[45] Mar. 27, 1979

[54] POWER HANDLE FOR HYDRAULIC TOOTHBRUSH-SPRAY APPLIANCE

[75] Inventors: Michel A. Moret, Chene Bourg; Pierre J. Jousson, Geneva, both of Switzerland

[73] Assignee: Les Produits Associes LPA, Geneva, Switzerland

[21] Appl. No.: 811,906

[22] Filed: Jun. 29, 1977

[30] Foreign Application Priority Data

Jul. 9, 1976 [CH] Switzerland .......................... 8814/76
Jul. 9, 1976 [CH] Switzerland .......................... 8815/76

[51] Int. Cl.² ............................................. A61H 7/00
[52] U.S. Cl. ..................................... 128/50; 15/22 R; 128/62 A
[58] Field of Search ........................ 128/50, 62 A, 66; 15/22 R, 22 C, 22 A

[56] References Cited

U.S. PATENT DOCUMENTS

| 3,536,065 | 10/1970 | Moret | 128/50 |
| 3,631,556 | 1/1972 | Holster et al. | 15/22 R |
| 3,771,186 | 11/1973 | Moret et al. | 15/22 R |
| 3,878,577 | 4/1975 | Jousson | 15/22 R |

Primary Examiner—Lawrence W. Trapp
Attorney, Agent, or Firm—Pennie & Edmonds

[57] ABSTRACT

A hand-held device for body care, in particular for tooth care and mouth care, which comprises a device casing serving as grip member, a hydraulic piston motor, an instrument holder alternatingly drivable by the motor, a liquid duct connectable to an external liquid pump, for feeding the hydraulic piston motor, and at least one adjustable valve for energizing and stopping the hydraulic motor. The device is adapted for use with treatment instruments which can be attached to the instrument holder in an interchangeable manner, in particular tooth brushes or spraying nozzles.

13 Claims, 11 Drawing Figures

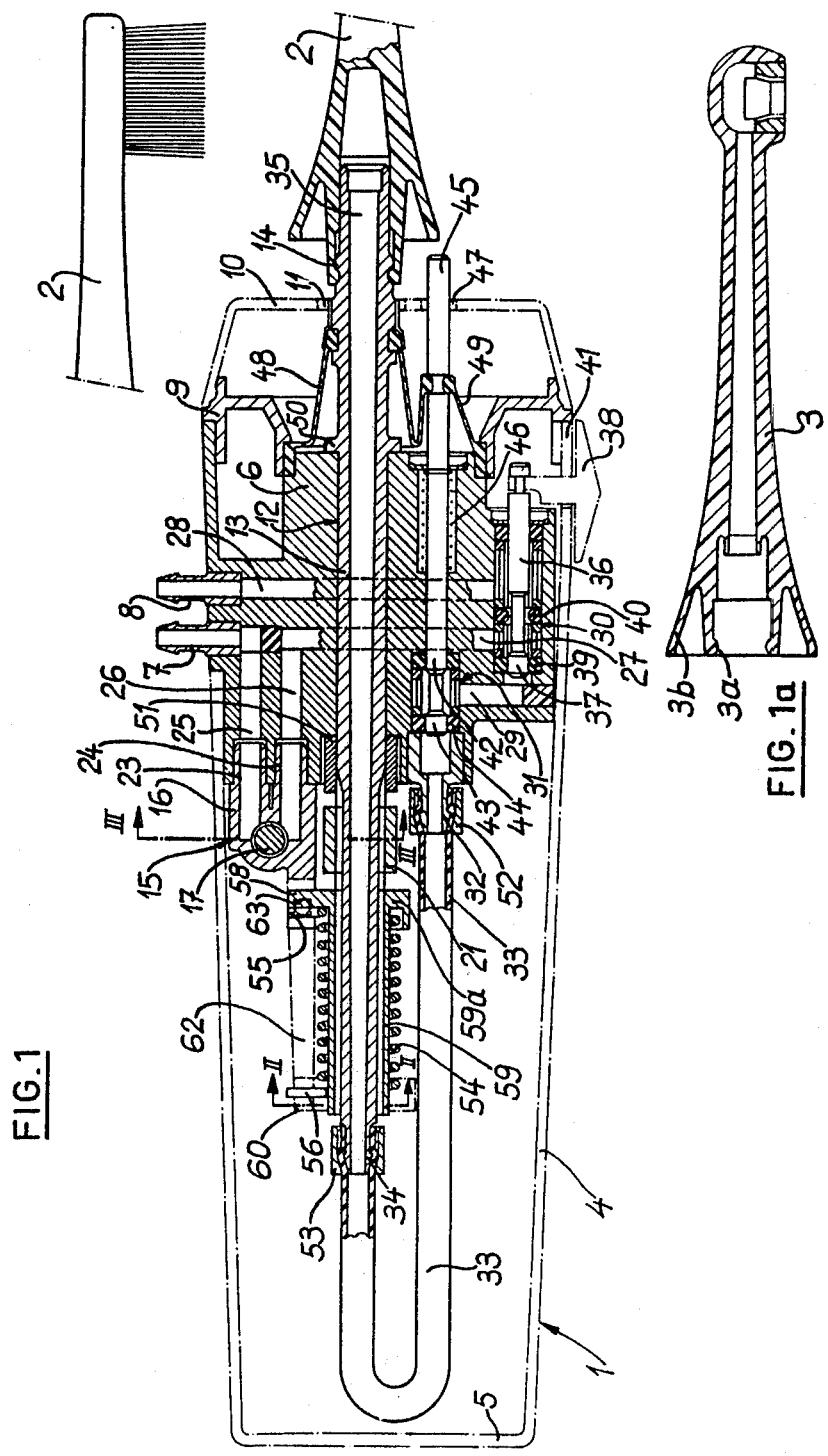

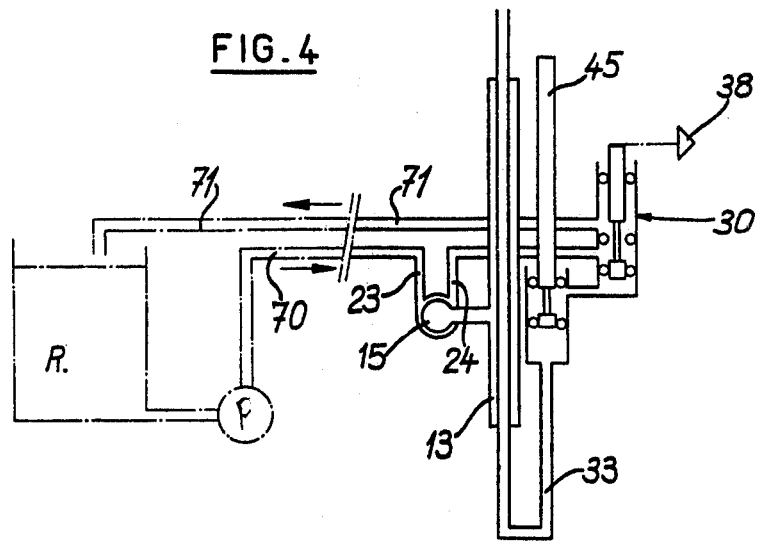
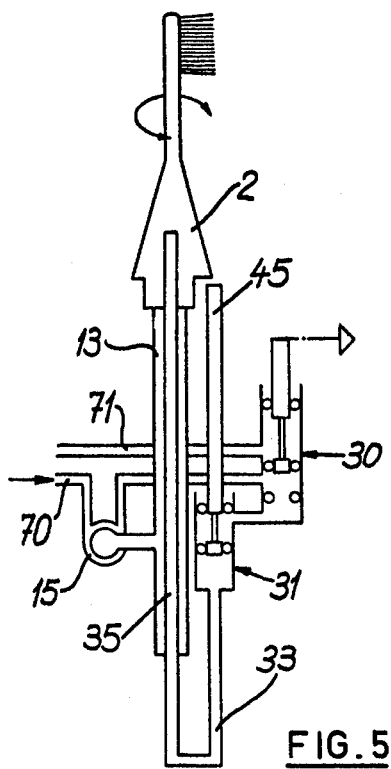
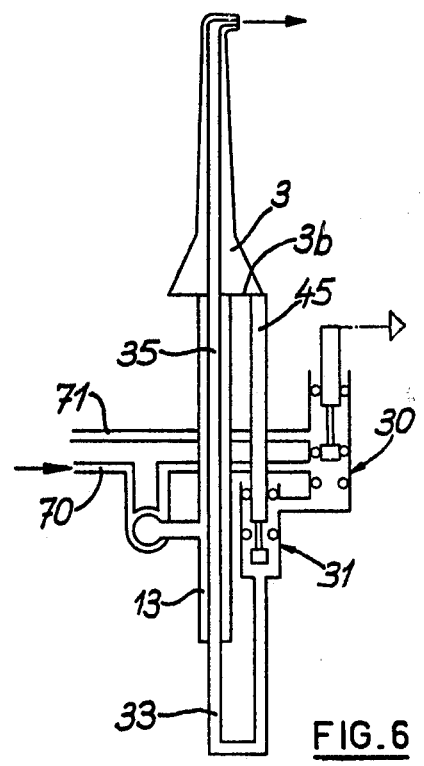

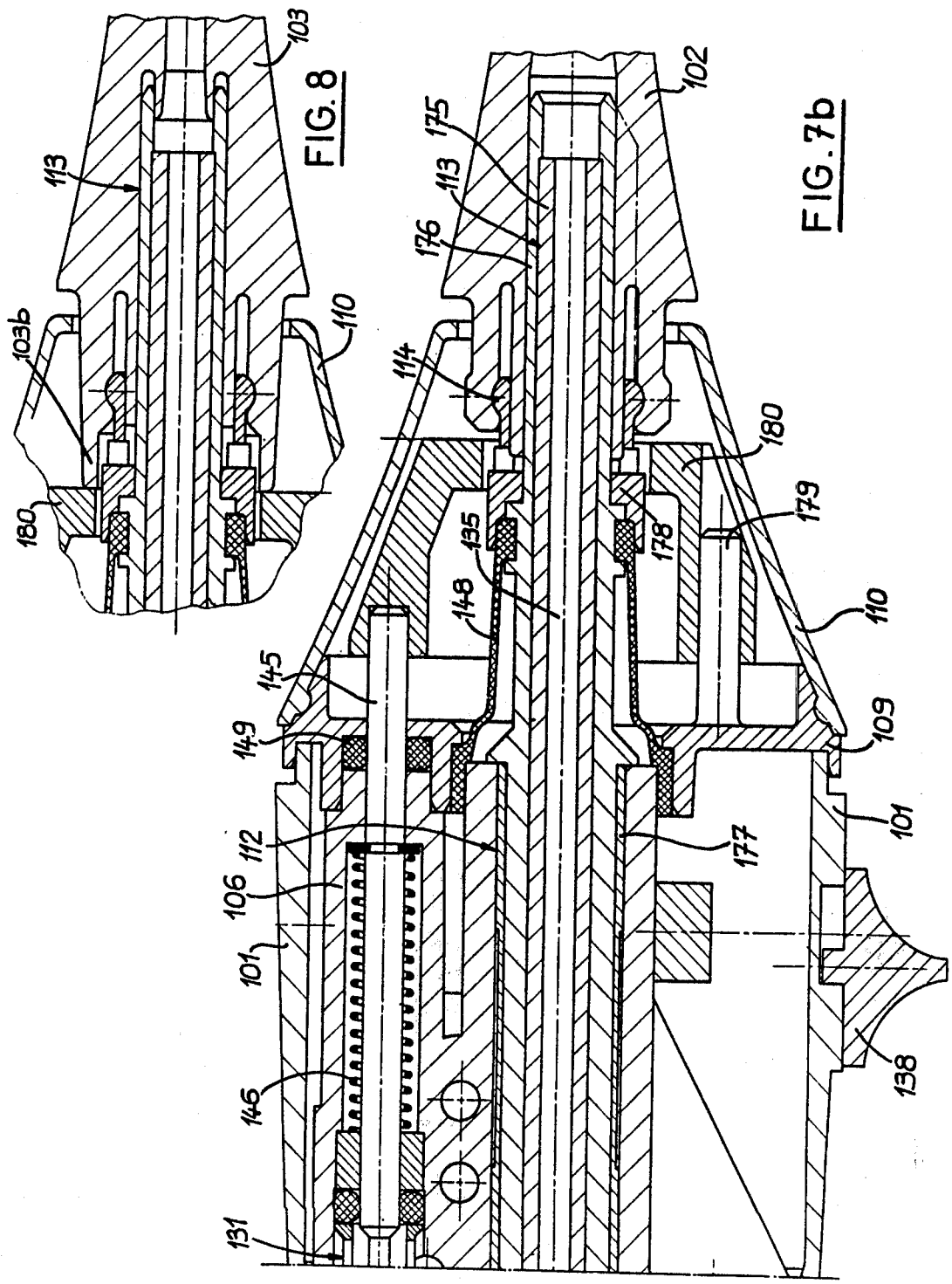

POWER HANDLE FOR HYDRAULIC TOOTHBRUSH-SPRAY APPLIANCE

BACKGROUND OF THE INVENTION

1. Field of the Invention

This invention relates to fluid-powered hand-held devices for body care, particularly for tooth care and mouth care.

2. Description of the Prior Art

In known hand-held devices of this kind, such as those disclosed in U.S. Pat. Nos. 3,536,065 and 3,771,186, the hydraulic piston motor is arranged concentric with or in the longitudinal axis of the device casing. During the operation of the hydraulic motor the piston thereof is reciprocatorily driven in the axial direction of the device casing by the pressure pulses produced by the liquid pump and sets the instrument holder into an oscillating rotary motion about its longitudinal axis by means of a motion converter. The hydraulic motor is inoperative when a pushed-on spraying nozzle is used which is fed through the liquid duct in the device casing.

One prior art motion converter consists of a driving sleeve which is freely rotatably, but axially non-displaceably mounted in continuation of the motor cylinder and has a helical groove provided in its peripheral wall; the leading end of the piston enters into the driving sleeve and supports a radial pin which engages into the helical groove and thus converts the axial reciprocatory motion of the piston into an oscillating rotation of the driving sleeve. Typically a pin and slot connection or a spring aim and detent connection are used for removably attaching the treatment instruments.

These known devices require a plurality of co-operating movable parts which cause abrasion effects and reduce the efficiency of the drive because of the motion converter and because of their mechanical friction. Furthermore in devices that include a motion converter the course of the feed pipe for the spraying nozzle in the device casing is rather complicated.

SUMMARY OF THE INVENTION

In accordance with this invention there is provided a hand-held device of the kind described above having a considerably simplified hydraulic piston motor which avoids a motion converter and permits the instrument holder or a shaft forming or supporting this instrument holder to be directly driven in an oscillating manner. This is achieved, according to the invention, in that the piston of the hydraulic motor is circularly curved in the stroke direction and is connected to a shaft which is mounted in the device casing and is rotatable about its longitudinal axis, wherein the rotary axis of the shaft penetrates the centre of the circle extending through the curved longitudinal piston axis and is disposed perpendicular to the plane of the circle, and that the piston is subjected to a return spring.

The invention has the great advantage that the piston of the hydraulic motor may be substantially rigidly connected directly to the shaft supporting the instrument holder, preferably by means of an arm formed on the outer end of the piston, so that the driving mechanism comprises only a single moved part and no centering or guidance for the piston is required in the motor cylinder.

Preferably the motor cylinder is also circularly curved in the stroke direction, like the piston, which is favourable in particular for reasons of space saving and for the purpose of avoiding superflous cylinder space, and the piston surrounded with play by the motor cylinder is sealed only at the end at which the piston issues from the cylinder, preferably by means of a sleeve. Alternately the motor cylinder may be constructed rectilinearly; in this case it must merely be dimensioned large enough in order to receive the curved piston. In either case the return spring for the piston consists preferably of a torsion-loaded helical spring which surrounds the shaft concentrically and the spring tension of which can be adjusted even after the assembly.

The oscillatory system formed by the piston and the shaft with the instrument holder as well as the return spring, with the liquid pump feeding the hydraulic piston motor being appropriately dimensioned, operates with an oscillation frequency of at least 20 Hz, preferably approximately 40–60 Hz. Under certain circumstances, even higher oscillation frequencies up to e.g. 100 Hz may be obtained. The piston oscillation is further considerably improved in this case by elastic abutments which define or limit the rest position and the maximum stroke of the piston.

The hand-held device according to the invention is preferably so arranged that it can be operated either with a push-on toothbrush driven by the hydraulic piston motor, or with a push-on spraying nozzle which upon adjustment of an appropriate valve, is fed through the hollow constructed instrument holder with the liquid stream delivered by the same external liquid pump used to provide liquid to the hydraulic piston motor. According to a further feature of the invention, the shaft comprising the instrument holder is constructed in this case as a hollow shaft the inner duct of which constitutes a section of the inner spraying nozzle feed pipe, and the rear end of this hollow shaft is connected to the section of the spraying nozzle feed pipe which extends in the casing body, by a flexible tube which is arranged in the device casing and is freely movable over at least a portion of its length. Thereby the important advantage is obtained that the instrument holder or the hollow shaft need not be mounted in sealing rings of any kind, but it is sufficient to arrange the shaft freely rotatable simply in a substantially smooth axial bore of the casing body, wherein this axial bore can be constructed sufficiently long for stable mounting. A long bearing bore is favourable in view of the fact that the driven toothbrush is often subjected to rather strong pressure in use.

Since no sealing rings are required for the hollow shaft, all problems are avoided which are connected with the friction and the ageing of the sealing rings as well as with the physical and chemical change of the sealing material by toothpaste and the like penetrating therein. The easy mobility thus obtained of the shaft improves considerably the oscillation behaviour so that the instrument holder can be driven with a high degree of efficiency.

Moreover, owing to the use of the hollow shaft and the tube for the spraying nozzle feed pipe the course of this liquid pipe within the device casing is simplified, superfluous internal spaces in which air inclusions could be formed, being largely avoided.

The inner connecting tube consists preferably not only of a flexible material, but also a sufficiently elastic material in such a manner that in the operation of a driven instrument it effects a certain additional resetting force, which has likewise been found advantageous for the oscillation behaviour of the whole oscillation system.

Although particularly designed for use with toothbrush and liquid jet heads, the appliance of the invention can be used with other types of attachments requiring an oscillating drive or liquid pressure pulse.

BRIEF DESCRIPTION OF THE DRAWINGS

FIG. 1 is a longitudinal section through the device casing of a hand-held device for tooth and mouth care with a push-on toothbrush attached and fitted with a hydraulic motor according to the invention;

FIG. 1A illustrates a spraying nozzle which can be attached to the device casing shown in FIG. 1 in place of the push-on toothbrush;

FIG. 4 is a diagrammatic illustration of the operation of the liquid pump during idling;

FIG. 5 is a diagrammatic illustration of the operation of the hand-held device when driving a toothbrush;

FIG. 6 is a diagrammatic illustration of the operation of the device with a spraying nozzle fed with a liquid;

FIGS. 7a and 7b are is an axial section through an alternative embodiment of the device of the invention with push-on toothbrush;

FIG. 8 shows the forward portion of the device casing shown in FIG. 7 with spraying nozzle.

DESCRIPTION OF THE PREFERRED EMBODIMENTS

Figure 3:
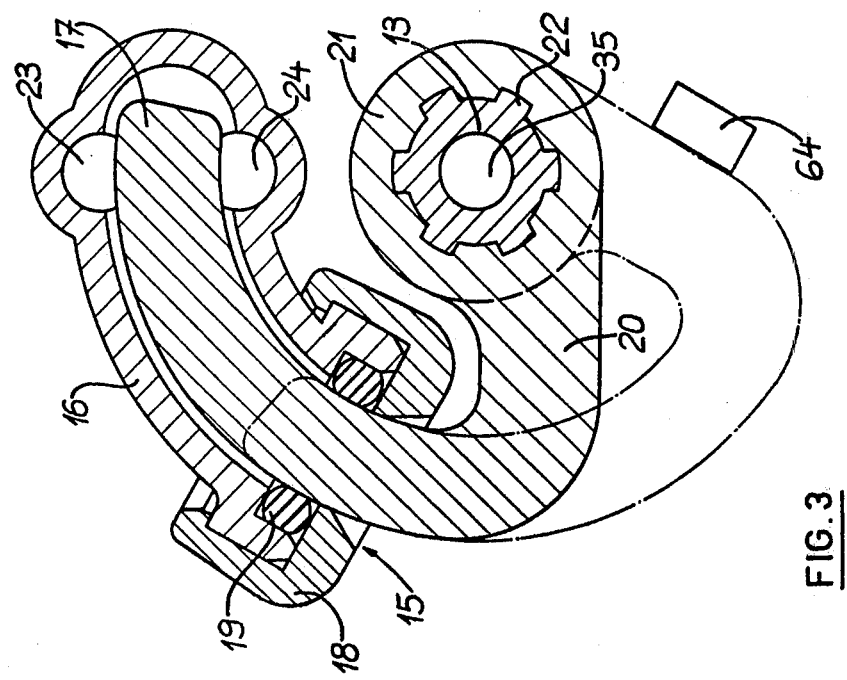
FIG. 3 is a section on the line III — III of FIG. 1 through the hydraulic motor.

Referring to FIG. 1 the device casing 1 serving as grip member is illustrated with a push-on toothbrush 2 attached thereto and comprises an outer casing sleeve 4 closed at the rear end 5 and a casing body 6 which is rigidly inserted in the forward region of casing sleeve 4 and has two connecting pipes 7 and 8 for the connection of flexible tubes (not illustrated) which form the liquid feed line and the liquid return line, respectively. These tubes connect the device casing to a liquid pump which is likewise not illustrated and which produces a pulsating liquid jet.

The forward end of the casing body 6 has attached thereto a circular flange 9 onto which a removable cover cap 10 is clamped with retention. A central bore 12 of the casing body 6 has a hollow shaft 13 mounted therein which is rotatable backwards and forwards about its longitudinal axis and the forward end 14 of which projects with free play through a central opening 11 of the cover cap 10. This forward end 14 of the hollow shaft 13 is provided with a detent profile for pushing thereon the toothbrush 2 or alternatively a spraying nozzle 3 such as illustrated in FIG. 1A. Thus the hollow shaft 13 forms the instrument holder.

The rear end of the casing body 6, adjacent the hollow shaft 13 has attached thereto the hydraulic motor 15 which will be described below in particular with reference to FIGS. 2 and 3; its piston 17 is directly and non-rotatably connected to the hollow shaft 13 and drives this hollow shaft 13 to oscillate about its longitudinal axis.

Liquid ducts 25, 26, 27, 28 and 29, a three-way valve 30 and a change-over shut-off valve 31 are disposed in the casing body 6. The duct 25 connects the inlet pipe 7 of the casing body to the inlet pipe 23 of the hydraulic motor 15, and the duct 26 connects the outlet pipe 24 of the hydraulic motor 15 to the duct 27 which, in the transverse direction of the device casing 1, extends past the central bore 12 to the inlet of the valve 30. The duct 28 which is disposed parallel to the duct 27 which connects one outlet opening of the valve 30 to the outlet pipe 8 of the device casing 1 and thus to a liquid return tube. The short duct 29 connects the other outlet opening of the valve 30 to the inlet of the change-over shut-off valve 31. A flexible tube 33 of elastic material is substantially freely movable within the casing sleeve 4 and connects the outlet pipe 32 of the valve 31 to the connecting pipe 34, constructed as part of the rear end of the hollow shaft 13. Fixing clips 52 and 53, respectively, ensure a sealed connection of the ends of tube 33 to the pipes 32 and 34, respectively. The inner duct 35 of the hollow shaft 13 terminates at the forward shaft end 14 and together with the tube 33 and the short duct 29 forms the liquid feed pipe for a spraying nozzle 3 pushed onto the forward end of the shaft 14. The valve 30 permits the hand-held device to be switched on and off while the liquid pump operates, and for this purpose the valve plunger 36 is adjustable together with the valve head 37 forming the closure member, by means of an outer slider member 38 which projects outwardly through an elongate slot 41 of the casing sleeve 4. In the position of the valve 30 illustrated in FIG. 1 the valve head 37 is located sealingly in a rear O-ring 39 and thereby shuts off the feed pipe to the short duct 29 and thus to the other valve 31, whereas the duct 27 is connected to the duct 28 through the O-ring 40 and therefore to the liquid return tube to the liquid pump. The device is therefore shown in the idling operating position, as will be described below with reference to FIG. 4. When the slider member 38 and together therewith the valve plunger 36 are pushed forwardly, the valve head 37 then is tightly engaged into the O-ring 40, shuts the liquid return pipe and permits liquid to pass from duct 27 to the short duct 29 and thereby to the valve 31.

Valve 31 also has a valve plunger 42 with a valve head 43 forming a closure member in co-operation with an O-ring 44. The valve plunger 42 has an actuator pin 45 which projects at the front through an opening 47 of the cover cap 10 and under the effect of a helical spring 46 assumes the position illustrated in FIG. 1 in which the valve head 43 is tightly engaged in the O-ring 44 closing the inlet pipe 32 to the tube 33 and thereby to the hollow shaft 13. With valve 31 in this position and when the valve 30 shuts the liquid return pipe, liquid powers the hydraulic piston motor 15 and thereby the push-on toothbrush is moved oscillatingly. When the actuator pin 45 is pressed in against the effect of the spring 46 and therefore the valve head 43 is displaced out of the O-ring 44, the access to the tube 33 and to the inner duct 35 of the hollow shaft is opened, so that then a spraying nozzle 3 attached at 14 can be fed. The two last-mentioned operative states of the device will be described in more detail with reference to the diagrammatic FIGS. 5 and 6.

In order to seal perfectly the locations where the hollow shaft 13 and pin 45 exit from the casing body 6 and simultaneously to ensure the necessary mobility of these elements, two truncated cone-shaped sealing sleeves 48 and 49 of a flexible material, for example rubber, are provided the forward ends of which are tightly clamped to the periphery of the hollow shaft 13 and the actuator pin 45, respectively, and the rear ends of which are tightly clamped between the casing body 6 and the flange 9. Preferably sealing sleeves 48 and 49 are constructed in one piece, as shown in FIG. 1. However, separate parts may be used.

Since the hollow shaft 13 is connected to the stationary casing body 6 by means of a flexible tube 33, no further seals of any kind need be present between this hollow shaft 13 and the casing body 6; in particular no O-rings are required in which this hollow shaft must be rotatable, so that the friction losses connected with such a shaft mounting are avoided. The axial displaceability of the hollow shaft 13 is limited by a formed-on forward shoulder 50 and a rear bush 51 located on the hollow shaft 13. Within the normal tolerances the axial displacement of hollow shaft 13 may amount to, for example, approximately 0.3 mm.

Referring now to FIG. 3, the hydraulic piston motor 15 comprises a piston 17 and a motor cylinder 16 which surrounds the latter with rather large play. Both the piston 17 and cylinder 16 are curved circularly in the stroke direction with their curved axes lying on a circle which is concentric with the longitudinal axis of the hollow shaft 13. A flange 18 fixed to the open cylinder end supports an O-ring 19 sealing the piston 17. The piston 17 is non-rotatably, but axially easily displaceably secured to the hollow shaft 13 by means of an integrally-formed arm 20 and sleeve 21 pushed onto the hollow shaft. The hollow shaft 13 has longitudinal ribs 22 which engage in axial grooves in the inner periphery of the sleeve 21. The axial mobility of the piston 17 permits automatic centering thereof in relation to the motor cylinder 16, so that in particular one-sided pressure against the O-ring 19 or even oblique positioning of the piston in the cylinder is avoided, when the hollow shaft 13 moves within its axial play and principally when it is pressed rearwardly by the contact pressure exerted by the user of a toothbrush. Thus the movement path and the position of the piston 17 are defined without special centering or guiding members by the sliding seat thereof on the hollow shaft 13, and tight manufacturing tolerances are not required.

The inlet and outlet openings of the motor cylinder 16 formed by integrally-formed inlet and outlet pipes 23 and 24, respectively, lie adjacent each other as shown in FIG. 3 at the inner cylinder end remote from the piston exit end, or are at least approximately disposed diametrically opposite each other. Naturally they may alternatively be disposed at or in the regions of the oppositely disposed cylinder ends. Liquid flow between the inlet and outlet openings occurs in all piston positions. In particular in the rest position of the piston 17 illustrated in FIG. 3 by cross-hatching flow is permitted by means of a ring space between the piston and the inner periphery of the cylinder. Since in this way the motor cylinder 16 forms a portion of the liquid pipe extending in the casing body 6 between the ducts 25 and 26, the piston 17 is always well covered with liquid and thus wetted, even during idling of the liquid pump and during feeding of a spraying nozzle, and likewise any possibly occurring air bubbles are removed thereby from the hydraulic piston motor 15. This is important in order to obtain a perfect start of the hydraulic piston motor 15 when the duct 29 is closed by the valve 30.

The pipes 23 and 24 which are oriented parallel to each other and perpendicular to the piston stroke and, for simple fixing of the motor cylinder 16 to the casing part 6, are pressed into appropriate openings in casing 6 so as to communicate with ducts 25 and 26, respectively.

Returning now to FIG. 1, the return spring used for the piston 17 is a helical spring 54 which is torsion-loaded and surrounds the hollow shaft 13 concentrically. For facilitating centering, spring 54 is disposed on a sleeve 59 mounted rigidly on the hollow shaft 13. This sleeve 59 has axial inner grooves and is non-rotatably secured to the region of the hollow shaft 13, provided with the longitudinal ribs 22 which engage the grooves.

Figure 2:
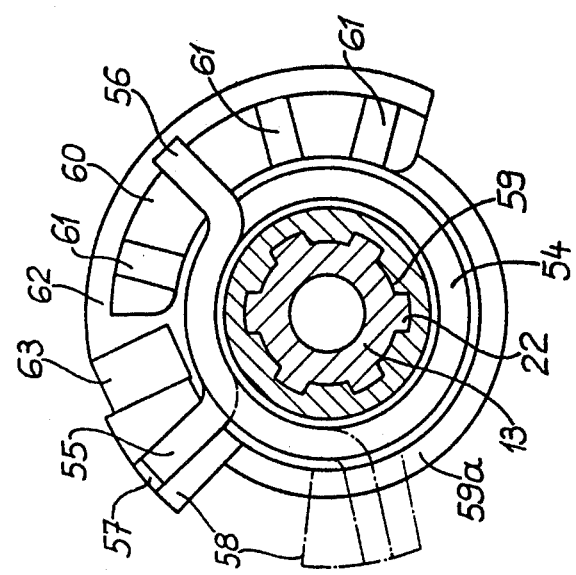
FIG. 2 is a section on the line II — II of FIG. 1.

Referring now to both FIGS. 1 and 2, the leading end 55 of spring 54 is radially bent away and engages in a radially directed groove 57 of a securing member 58 which is formed by a radial projection at the forward flange 59a of the sleeve 59, and is therefore non-rotatably connected to the hollow shaft 13. The flange 59a has a ring groove for receiving the forward spring region. The rear end 56 of spring 54 which is also radially bent away is secured against displacement in the circumferential direction by a securing member 60 which is formed on an arm 62 rigidly connected to the casing 6 or alternatively the motor cylinder 16. This securing member 60 surrounds arcuately the helical spring 54 which is not pre-tensioned in the axial direction, over a portion of the periphery thereof and comprises on its back side remote from the forward spring end 55 a plurality of radially directed grooves 61 which are disposed at a mutual angular spacing and into which the spring end 56 is selectively insertable. By suitably selecting a radial groove 61 for receiving spring end 56 the pre-tensioning of the spring 54, i.e. its torsion tension, can be conveniently adjusted even after assembly. Therefore the characteristics of spring 54 need not be specially selected in order to achieve the desired operating characteristics of the device.

Referring now to FIGS. 1 and 3, the stroke of the piston 17 is limited in both directions by stationary abutments 63 and 64 which are preferably rubber buffers, to minimize noises and hard piston impacts. The abutment 63 (FIG. 2) fixed to the arm 62 co-operates with the securing member 58 and defines the rest position of the piston 17, illustrated by cross-hatching in FIG. 3. Also shown in FIG. 3 is the abutment 64 which is fixed to the casing body 6, defines the maximum working stroke of the piston 17, as illustrated by dash-dotted lines, and serves substantially as a safety limit. In normal motor operation it should not be touched by the piston or, when the motor runs without load, at most lightly.

The helical spring 54 is pretensioned such that the force retaining the piston 17 in its rest position shown in FIG. 3 is sufficient to avoid a movement of the piston under the effect of the pulsating liquid when the device is operated without load or with a spraying nozzle 3. When the hydraulic motor 15 is in operation, the working stroke of the piston 17 is effected by a pressure pulse delivered by the liquid pump against the effect of the spring 54 which thereafter during the following pressure pause returns the piston again to its rest position. In the present example the maximum working stroke of the piston 17 amounts to approximately 60°.

Referring now to FIGS. 4, 5 and 6 which illustrate diagrammatically the three operational states of the hand-held device. In FIG. 4 the liquid pump P and its water reservoir R are also diagrammatically indicated. The pump outlet is shown connected directly to the inlet pipe 23 of the hydraulic motor 15 by the liquid feed tube 70. Whereas in fact the tube 70 would connect to inlet pipe 7. Similarly the liquid return pipe 71 which terminates in the liquid reservoir R or at the inlet of the pump P as shown connected directly to valve 30. Whereas in fact it would connect to pipe 8. In FIG. 4 the valve 30 is shown in the OFF-position in which it connects the liquid feed pipe 70 to the liquid return pipe 71 by way of the cylinder chamber of the hydraulic motor 15, that is to say the inlet tube 23 and the outlet tube 24 of the hydraulic motor, by way of the ducts 27 and 28 of the casing part 6 as shown in FIG. 1. Since the pump circuit is thus short-circuited in the sense of the arrows by way of the device casing, substantially no pressure can be built up in the hydraulic system, the hydraulic motor 15 remains inoperative and the liquid delivered by the pump flows to the reservoir R or back to the pump inlet. At the same time the hydraulic system, in particular the hydraulic motor lying in the liquid pipe, is de-aerated.

Referring now to FIG. 5 the valve 30 is shown in the ON-position in which the liquid return pipe 71 is closed. Under the effect of its spring valve 31 is closed and interrupts the connection to the tube 33. Since the liquid travelling from the pump through the feed pipe 70 to the hydraulic motor 15 cannot flow away, the hydraulic motor 15 is driven, its piston 17 swinging to and fro in the rhythm of the pulse succession frequency of the liquid and under the effect of the return spring 54. Therefore the push-on toothbrush located on the driven hollow shaft 13 oscillates about its longitudinal axis in the direction of the double-arrow. With the exception of leakage losses, substantially no liquid is lost thereby; the liquid column present in the liquid pipe between the pump and the hydraulic motor 15 merely swings to and fro. Thus the pump P operates in this case substantially as a pressure transmitter.

When the hydraulic motor 15 is in operation, the running liquid pump, the outer connecting tube 70, the hydraulic motor, the moved liquid as well as all mechanically moved parts form an oscillatory system which under load is designed to operate at least approximately at its resonant frequency in order to obtain a sufficient degree of efficiency of the hydraulic motor and a sufficient piston stroke and thereby a sufficient oscillatory movement of the toothbrush 2. There are numerous factors which determine the resonant frequency of this system which must therefore appropriately select for its tuning. These factors include the helical spring 54 and, to a lesser degree, the tube 33, provided its material is not only flexible but preferably also sufficiently elastic. In addition to the return force of the helical spring 54, the elastic return force of the tube 33 subjected to forward and backward torsion acts then also in this case to a minor degree on the oscillating hollow shaft 13. When the oscillatory system referred to has been tuned coarsely by a suitable choice of the factors which determine the resonant frequency, fine tuning is still possible after the assembly of the major parts of the device in a simple manner by means of the helical spring 54 and tube 33, which is very advantageous. As already described, the torsional tension of the helical spring 54 can be changed by the selection of an appropriate groove 61 for the spring end 56, whereas the return force exerted by the tube 33 is variable by simply changing the tube dimensions, in particular the tube length.

Furthermore, in order to prevent the oscillation amplitude of the oscillatory system and thus the stroke of the piston 17 from increasing too much in the unloaded state of the hydraulic motor as compared with the loaded state, that is to say when the user presses the toothbrush against the teeth, a suitably dimensioned damping of the oscillating parts is important. This necessary damping is produced in a simple manner by the flexible sleeve 48 which is twisted to and fro during the oscillation of the hollow shaft 13 and the material of which is selected thickness and size accordingly. In this manner, the most desirable oscillation amplitude of the system can be attained and thus the stroke of the piston 17 in the unloaded state of the hydraulic motor is at most 30% greater than when under load and therefore the piston 17 touches the abutment 64 (FIG. 3), if at all, with a weak impact.

Referring now to FIG. 6, the valve 30 is again in the ON-position, whereas the valve 31 is displaced by the pushed-on spraying nozzle 3 into that position in which the liquid feed pipe 70 is connected through the cylinder chamber of the hydraulic motor 15 to the tube 33 and thus to the inner duct 35 of the hollow shaft 13. For this purpose, as illustrated in FIG. 1A, the spraying nozzle 3 has an abutment 3b which projects radially outside its plug profile 3a and which is constructed in the form of a flange concentrically surrounding this plug profile 3a. The abutment 3b co-operates with the actuator pin 45 in such a manner that this actuator pin 45 and thus the valve plunger 42 is displaced into its depressed inner position against the effect of the valve spring 46 when the spraying nozzle 3 is attached. In this position the hydraulic motor 15 is inoperative, the sufficient pre-tension of the helical spring 54 preventing a piston movement under the reduced effect of the liquid pulses, and the spraying nozzle 3 is connected to the external liquid pump, so that a pulsating liquid jet issues from the spraying nozzle in the direction of the arrow in FIG. 6. The user need not pay attention to a valve change-over upon changes from 'brush operation' to 'spraying nozzle operation', since as described this change-over occurs automatically when the spraying nozzle 3 is attached. Upon removal of the spraying nozzle the valve 31, under the effect of its valve spring 46, automatically assumes its position corresponding to 'brush operation' as shown in FIG. 5. The rear end of the push-on toothbrush 2 is so constructed that in the pushed-on position it does not contact the actuator pin 45.

Due to the direct oscillating drive of the hollow shaft with the toothbrush, not only are friction and abrasion effects that occur in a motion converter avoided; but also the oscillatory system which comprises substantially only one common moved part oscillates in an impact and shock-free manner. Moreover the mechanical construction is very simple so that the hand-held device is economical to produce, for example, the motor cylinder and the piston with its fixing sleeve may be inexpensive components molded of synthetic resin.

Finally, since the driven shaft is a hollow shaft and constitutes directly a rectilinear section of the liquid feed pipe to the spraying nozzle, a simple and direct guidance of the liquid in the device casing is obtained and so-called dead spaces and air inclusions connected therewith are avoided.

Figure 7A:
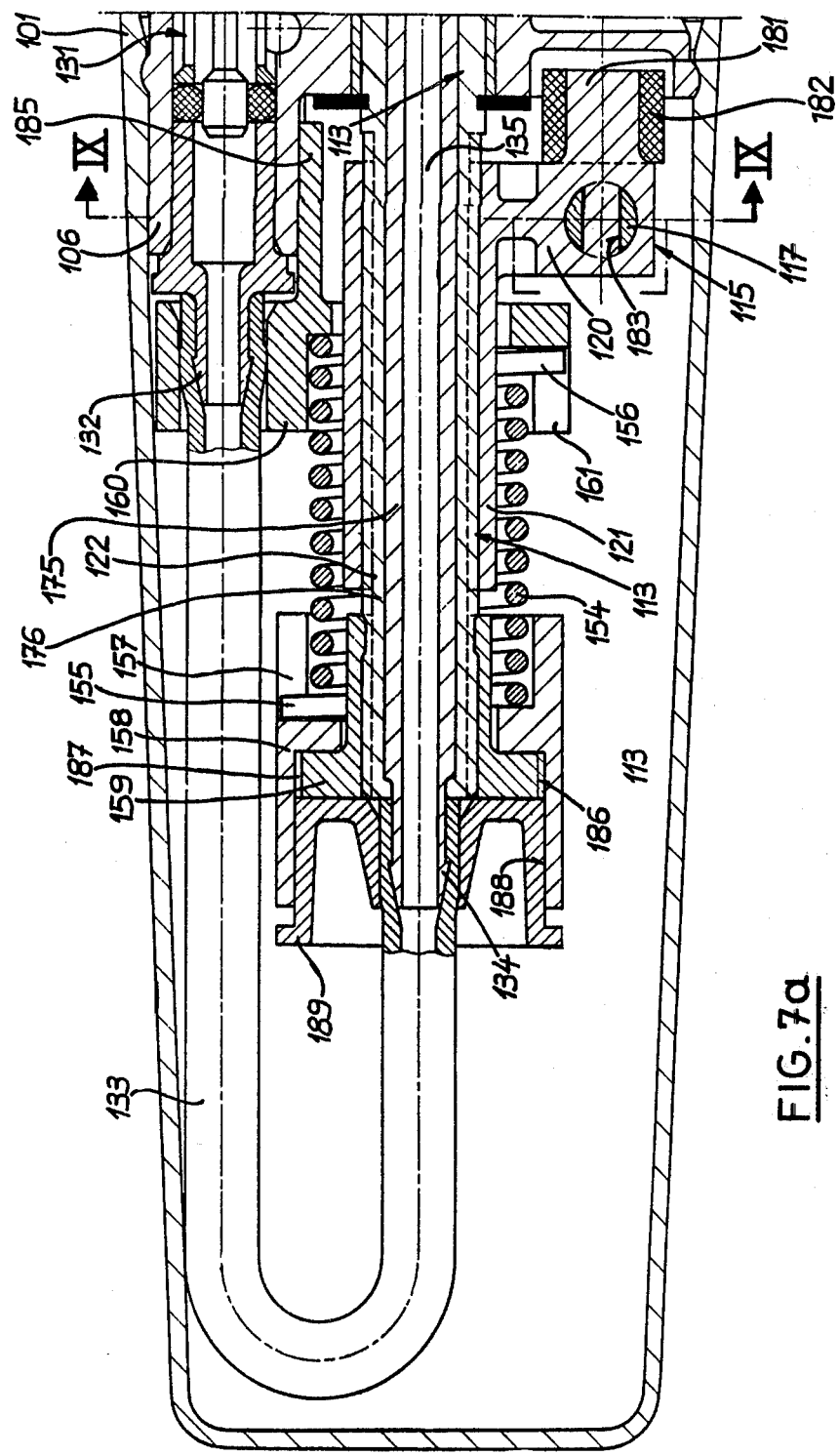

An alternative embodiment of the device of the invention is shown in FIGS. 7a, 7b, 8 and 9. Referring to FIG. 7a and 7b the hand-held device again comprises an elongate device casing 101 and a casing body 106 in which a valve with an outer actuator element 138, corresponding to the three-way valve 30 in the first example, and a change-over shut-off valve 131 operating corresponding to the shut-off valve 31 in the first example, are mounted. In this embodiment the valve 131 is located approximately diametrically opposite the three-way valve. The hollow shaft 113 is mounted in the central bore 112 of the casing body 106 and consists of an inner metal tube 175 of stainless steel and a synthetic resin jacket 176, for example of an acetate resin. In the region of its bearing the hollow shaft 113 is provided with a metal sleeve 177 pressed thereon. The rear connecting pipe 134 of the hollow shaft 113 is again connected to the pipe 132 of the change-over valve 131 by means of a flexible freely movable tube 133. The forward end of the hollow shaft 113 supports a sleeve-like member 178 which serves for clamping the forward end of an elastic sealing sleeve 148 and has at the front a detent profile 114 for attaching a push-on toothbrush 102 or a spraying nozzle 103 (FIG. 8). The forward end of the casing body 106 has a flange 109 attached thereto which clamps the rear end of the sealing sleeve 148 against the casing body 106 and on which a cover cap 110 is retained.

Within the cover cap 110 an axially freely movable cup-shaped slider member 180 is mounted on a guide pin 179 of the flange 109. The actuator pin 145 of the change-over valve 131 engages in an inner opening of the slider member 180 which is not engaged by the plug of a pushed-on toothbrush 102, but is pushed back (FIG. 8) during attachment of a spraying nozzle 103 by the axially rearwardly elongated projection 103b of the nozzle plug, which causes displacement of the actuator pin 145. As in the first example, during attachment of a spraying nozzle 103 the change-over valve 131 is displaced in this way against the effect of its valve spring 146, such displacement being effected by means of the slider member 180 into the position which corresponds to the feeding of the spraying nozzle. In the present embodiment, the actuator pin 145 is located outside the sealing sleeve 148 and is sealed by an O-ring 149.

Figure 9:
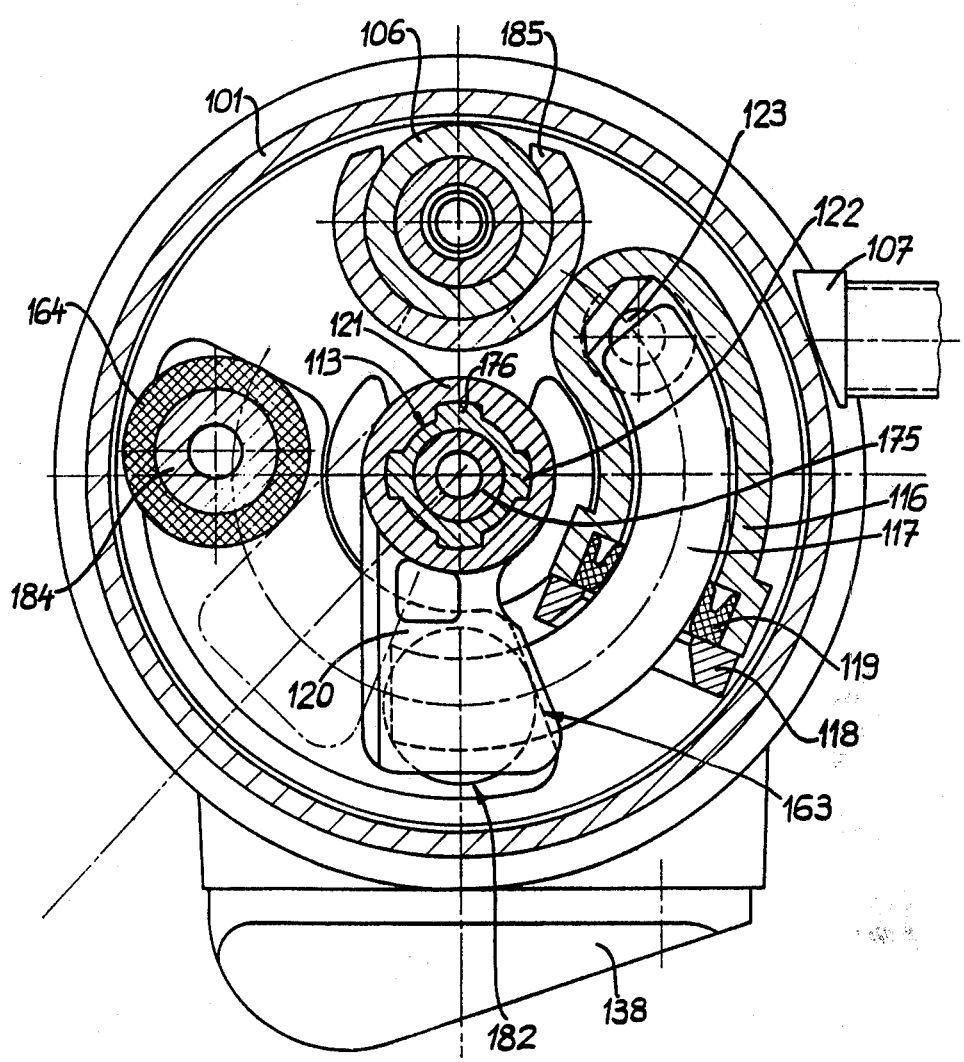
FIG. 9 is a section on the line IX — IX of FIG. 7.

Referring now to FIG. 9 the curved cylinder 116 of the hydraulic motor 115 consists of synthetic resin and is secured to the casing body 106, in this case it has at the rear end only a single lateral feed pipe 123 which is connected through a single duct to the liquid inlet pipe in the casing body, corresponding to the duct 25 shown in FIG. 1. Thus the outlet tube 24 and the duct 26 of FIG. 1 are omitted. It is sufficient that the cylinder 116 is connected through a single pipe to the feed pipe coming from the external liquid pump, which in the example shown in FIG. 1 this is the duct 27 leading from the casing connecting tube 7 to the three-way valve 30. It has been found that even in this simplified construction the hydraulic motor operates perfectly and that substantially no air inclusions are formed in the cylinder and its feed pipe. The casing connecting tubes, corresponding to the tubes 7 and 8 of FIG. 1, as well as the ducts in communication therewith and extending through the casing body, to the motor cylinder 116 as well as to the three-way valve corresponding to the valve 30 in FIG. 1, and to the change-over valve 131 are not shown in detail in FIGS. 7a and 7b.

The circularly curved motor piston 117 consists of a curved metal pin of circular cross-section, is arranged with play in the cylinder 116 and sealed at the outer cylinder end by a sealing sleeve 119 which is retained by a flange 118 fixed to the cylinder. The outer end of the metal piston 117 is embedded in a synthetic resin component, for example glass-reinforced polyester, which forms a radial arm 120 with an attachment 181 parallel to the hollow shaft 113 (FIG. 7a) and a fixing sleeve 121 which is non-rotatably mounted on the hollow shaft 113, but is axially easily displaceable thereon. Again, as in the first example, longitudinal ribs 122 are provided on the synthetic resin jacket 176 of the hollow shaft 113 which engage corresponding longitudinal grooves in the inner periphery of the sleeve 121. Referring again to FIG. 7a, the fixing sleeve 121 supporting the piston has a relatively great axial length, which ensures a good sliding seat for the piston. At its casting location the metal piston 117 has a transverse opening 183 (FIG. 7a) which during casting is penetrated by synthetic resin and ensures a particularly stable connection to arm 120. The attachment 181 of the synthetic resin component is surrounded by a rubber buffer 182 which in the inner position of the piston illustrated in FIG. 9 abuts against the casing abutment 118 and thereby defines the rest position of the piston. The maximum stroke of the piston which is about 45° in the present embodiment is limited by an elastic stationary abutment in the form of a rubber buffer 164 pushed over a casing pin 184; the piston arm 120 impinges upon this buffer which, in order to prevent a possibly occurring tilting of the piston upon hitting the abutment, lies in the plane of the circle defined by the curved piston or at least approximately in the continuation of the curved longitudinal piston axis. The maximally displaced piston abutting the rubber buffer 164 is illustrated by a dash-dotted line in FIG. 9.

The casing pin 184 is formed on an inner casing part 185 which on the one hand embraces partly a tubular attachment of the casing body 106 receiving the valve body of the valve 131, and on the other hand comprises the cup-shaped fixing member 160 (FIG. 7a) for the stationary end 156 of the helical spring 154 which is the return spring for the piston 117 and which surrounds with play the hollow shaft 113 and the fixing sleeve 121. To fix the spring 154 the radially bent spring end 156 engages in a radial groove 161 of the fixing member 160.

The other end 155 of spring 154 which is likewise radially bent away is secured to a fixing member 158 which is connected to the hollow shaft 113, and which has a radial groove 157 which is engaged by the spring end 155. This fixing member 158 which surrounds the spring 154 like a cup sits on a sleeve 159 which is pressed on to the rear end of the hollow shaft 113, the longitudinal ribs 122 of the hollow shaft engaging into corresponding axial grooves in the inner periphery of the sleeve 159. The fixing member 158 comprises an axially rearwardly extending ring flange the inner periphery of which has internal teeth 186 meshing with peripheral teeth 187 of the sleeve 159; a smooth peripheral region 188 follows rearwardly. A flange 189 which ensures the fixing of the tube 133 on the connecting pipe 134 of the hollow shaft 113 engages into the rear smooth region of the inner periphery of the fixing member 158.

In this embodiment the fixing of the spring end 155 permits in a simple manner the pre-tension of the helical spring 154 which in operation is torsionally loaded, to be adjusted after the assembly, in that the fixing member 158, with the flange 189 removed, is displaced forwardly on the hollow shaft 113 while compressing the spring 154 until its internal teeth 186 are disengaged from the teeth 187 of the sleeve 159, whereupon the fixing member 158 together with the spring end 155 engaging into the groove 157 can be rotated in one direction or the other by one or more teeth of the teeth referred to with a corresponding change of the torsion pre-tension. Thereafter the fixing member 158 is merely displaced into its normal position shown in FIG. 7a. in which it is non-rotatably fixed on the hollow shaft 113 by the meshing of the teeth 186 and 187.

The hand-held device of this embodiment is so constructed that, in operation, the piston 117 of the hydraulic motor 115 abuts with some force the abutments limiting its stroke elastically which not only damps noises, but also contributes to the improvement of shock-free oscillation. When the external liquid pump is appropriately dimensioned, the arrangement may be made so that the motor piston with the hollow shaft and the driven instrument oscillates at a frequency of at least 20 Hz, preferably between 40 and 60 Hz, wherein when the electro-motor driving the hydraulic pump rotates preferably for example at a speed of 3000 revs/min, the toothbrush is driven during idling of the hand-held device at a speed of 50 Hz, this being particularly favourable for the massage of the gums.

It will be apparent to those of ordinary skill in the art that changes may be made in the above-described specific preferred embodiments without departing from the scope and spirit of the invention, which is limited solely in accordance with the following claims.

We claim:

1. A hand appliance for body care for use with instrument heads requiring alternatively rotational oscillation and liquid pressure pulses, and driven by a source of liquid pressure pulses comprising:
   (a) an elongated casing forming a handle;
   (b) support means mounted in said casing for axially supporting a hollow output shaft;
   (c) said shaft having retaining means for co-operating with detent means of an instrument head and retaining the head on said shaft;
   (d) flexible conduit means for connecting said casing and support means with said source of liquid pressure pulses;
   (e) hydraulic piston motor means for rotationally oscillating said shaft about its longitudinal axis;
   (f) said motor means having a piston circularly curved in the stroke direction connected to said shaft such that its circularly curved longitudinal axis is concentric with and perpendicular to the longitudinal axis of said shaft;
   (g) spring means for returning said piston in one direction of its stroke;
   (h) conduit means with first valve means in said support means for connecting said flexible conduit means to said hydraulic piston motor and for starting and stopping said motor;
   (i) manually actuable control means for controlling said first valve means;
   (j) conduit means with second valve means in said support means for connecting said flexible conduit means to said hollow output shaft; and
   (k) control means for controlling said second valve means such that liquid pressure pulses are delivered through said hollow shaft when an instrument head requiring liquid pressure pulses is retained on said shaft.

2. A hand appliance as defined in claim 1 wherein said flexible conduit means includes supply and return conduits and said conduit means in said support means includes input and return conduits connected respectively to said supply and return conduits.

3. A hand appliance as defined in claim 1 the rotation oscillation of which is resonant at least at a frequency of 20 Hz.

4. A hand appliance as defined in claim 1 the rotational oscillation of which is resonant at a frequency of between 40 and 60 Hz.

5. A hand appliance as defined in claim 1 wherein said hydraulic piston motor has a circularly curved cylinder surrounding said piston which is sealed only at the piston outlet end and which has an inlet opening at its opposite.

6. A hand appliance as defined in claim 5 wherein said piston is axially displaceable along said shaft whereby said piston is self centering.

7. A hand appliance as defined in claim 5 wherein the rest position and maximum stroke of said piston are defined by elastic abutments.

8. A hand appliance as defined in claim 1 wherein said spring means is a helical spring surrounding said shaft, one end of which is fixed to said shaft and the other end of which is adjustably retained by the support means.

9. A hand appliance as defined in claim 6 wherein said adjustable retention comprises angularly spaced grooves in said support means into which said spring end can be inserted thereby adjusting the torsion pretension of said helical spring.

10. A hand appliance as defined in claim 6 wherein said adjustable retention comprises a sleeve having peripheral teeth fixed to said shaft and a cup shaped member, to which said spring end is attached, having internal teeth for nonrotatable engagement with said peripheral teeth whereby the torsion pretension of said spring is adjusted by axially disengaging said teeth, rotating said member and reengaging said teeth.

11. The combination of a hand appliance as defined in claim 1 and a toothbrush instrument head.

12. The combination of a hand appliance as defined in claim 1 and a spray nozzle adapted to actuate said second valve control means.

13. A hand appliance as defined in claim 1 wherein said conduit means connecting said flexible conduit means to said hollow output shaft includes flexible conduit means.

* * * * *